United States Patent
Kossoff

[11] 3,990,300
[45] Nov. 9, 1976

[54] MOVING ULTRASONIC TRANSDUCER ARRAY
[75] Inventor: George Kossoff, Northbridge, Australia
[73] Assignee: The Commonwealth of Australia, Phillip, Australia
[22] Filed: Feb. 20, 1975
[21] Appl. No.: 551,300

[30] Foreign Application Priority Data
Feb. 21, 1974 Australia............... 6675/74

[52] U.S. Cl. .............................. 73/67.85
[51] Int. Cl.² ............................ G01N 29/04
[58] Field of Search ........... 73/67.5 R, 67.7, 67.8 R, 73/67.85, 67.9, 71.5 US; 128/2 V, 2.05 Z

[56] References Cited
UNITED STATES PATENTS

| 3,577,772 | 5/1971 | Perilhou et al. ............... 73/67.7 |
| 3,593,569 | 7/1971 | Wilson ........................... 73/67.7 |
| 3,741,004 | 6/1973 | Posakony ....................... 73/67.8 S |
| 3,802,253 | 4/1974 | Lee................................ 73/67.9 |
| 3,895,685 | 7/1975 | Gillette et al. ................ 73/67.8 X |

Primary Examiner—Richard C. Queisser
Assistant Examiner—Stephen A. Kreitman

[57] ABSTRACT

An apparatus for the pulse-echo ultrasonic examination, particularly in medical diagnostic examination, is comprised of a plurality of transducers spaced around the object to be examined, each of the transducers being steerable to direct pulses of ultrasonic energy into the object and to receive echoes in a plurality of angular directions, and means to move the plurality of transducers relative to the object during examination of the object.

14 Claims, 7 Drawing Figures

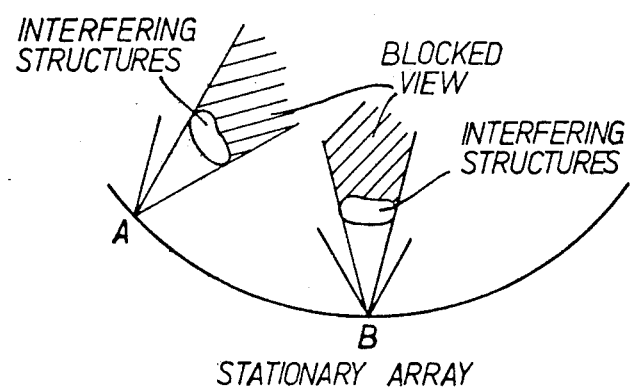
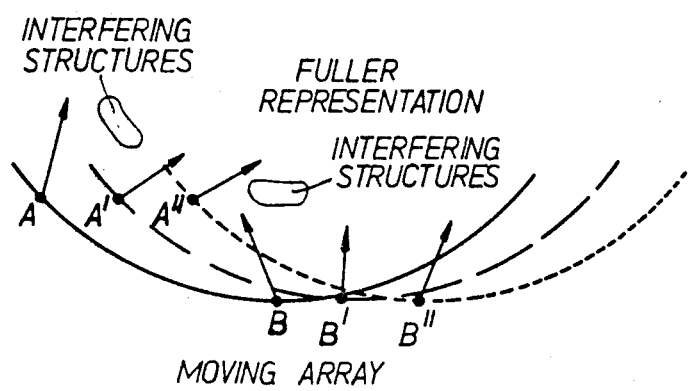
FIG.2.

MOVING ULTRASONIC TRANSDUCER ARRAY

Applicant has filed U.S. Patent application Ser. No. 368,357 directed to the use of a plurality of transducers in ultrasonic examination, such application having been filed on June 8, 1973, entitled "ULTRASONIC TRANSDUCER ARRAY," now U.S. Pat. 3,939,696.

This invention relates to the technique of ultrasonic echoscopy of objects and in particular to means for decreasing the time required for examination of an object using the pulse-echo ultrasonic technique and for improving the clarity and hence the utility of the examination results. It is particularly, but not solely, directed to the use of this technique in medical diagnostic examination.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line or as an intensity change. In a two dimensional display, the position along a base line is used to indicate the distance to the reflecting surface as in a one dimensional display, and the direction of the baseline is used to represent the direction or propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. The application of this technique is now widely investigated and is described, for example, by D. E. Robinson in Proceedings of the Institution of Radio and Electronics Engineers Australia, Vol. 31, No. 11, pages 385 – 392, November, 1970 : "The Application of Ultrasound in Medical Diagnosis." As pointed out in this article, ultrasonic echoscopy may be used to produce displays resembling anatomical crossections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients' condition, however, particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

In one presently known form of ultrasonic diagnostic examination, a single transducer is used and it is physically moved to various positions around the patient. At each of these positions the beam is swept with an oscillatory motion while constrained to remain within a single plane by mechanical oscillation of the transducer, to obtain the required scan pattern. By the use of suitable deflection circuits, for example, in a cathode ray display tube, a line is caused to follow the motions of the beam axis and echoes within the part examined are thus displayed in their correct geometrical positions. By way of example, for transverse sections, the transducer may be moved horizontally in a 150° arc around a patient who is substantially erect while undergoing ± 15° oscillations and for longitudinal sections the transducer may be moved vertically while undergoing ± 30° oscillations.

It has, however, been found that in such systems where the transducer is physically moved around the patient this movement leads to a limitation on the examination time of between ten and twenty seconds for each cross-sectional visualisation due to mechanical inertia and, in the case where the transducer is coupled to the patient via a coupling medium such as water, the generation of turbulance by the transducer when it moves quickly in the coupling medium.

Several alternative forms of ultrasonic examination equipment have been devised which will avoid the limitations discussed above and thus enable a speeding up of the time required for each cross-sectional visualisation. It will be apparent that a reduction in examination time of a patient will lead to a technical improvement in the resultant echograms as the effects of movement of the part under examination will be reduced. In addition, a reduction in examination time of a patient will have the economic advantage that more cross-sectional visualisations and hence more examinations will be able to be performed in a given time.

It has been found that the time taken for the ultrasonic examination of an object may be reduced by using an ultrasonic transducer array in which a number of transducers are used instead of the single transducer used previously. In a typical operation the transducers are energised sequentially, the time of energising each of the transducers being set so that the whole set of transducers is energised before the appropriate beam from each transducer has moved a significant distance on the display. In this way the entire scanned cross-section may be formed in one cycle of the transducers.

Such a transducer array, however, exhibits several disadvantages whilst overcoming the problem of the time necessary for physical movement of a single transducer. With a stationary array the lines of sight originate from fixed spatial position of the array. This limits the directions of the lines of sight used to examine an object and it becomes difficult to visualize structures if some intervening structure lies between one or more of the transducers and the examined object. For example, the ribs which overlie the liver may interfere with ultrasonic examination of that organ. Further, with a stationary array the combination of lines of sight from fixed origin gives rise to a background pattern consisting of bright and dark areas which interferes with the appearance of the display obtained from the echoes of reflected ultrasonic beams.

It is accordingly an object of the present invention to provide apparatus for and a method of ultrasonic examination of an object whereby the above mentioned disadvantages are avoided.

According to the present invention there is provided apparatus for the ultrasonic examination of an object comprising a plurality of transducers, each transducer being capable of directing pulses of ultrasonic energy along a beam into the said object and receiving echoes of said pulses reflected along said beam by acoustic impedance discontinuities in said object, the said transducers being spatially positioned in a single plane relative to each other and to the said object and the beam from each transducer being steerable to a plurality of angular directions in said plane, and means for moving said plurality of transducers in said plane relative to said object during examination of the object.

In another aspect, the invention provides a method of ultrasonic examination of an object which comprises directing pulses of ultrasonic energy along a plurality of beams into said object and receiving echoes of said pulses reflected along said beams by acoustic impedance discontinuities in said object, the said beams being directed into the object from positions spaced relative to each other in a single plane and each beam being steerable to a plurality of angular directions in said plane, and the positions from which said beams are directed being moved in said plane relative to said object during examination of the object.

It will be apparent that the present invention utilises a number of transducers instead of the single transducer used in some previous ultrasonic examination techniques. These transducers may be any type of electro-mechanical transducers, and suitable transducers are well known in the art.

The beam axes of the plurality of transducers of the present invention must be oscillated in order that a composite cross-sectional visualisation can be built up and this oscillatory motion may be provided by two alternative means. The first means of obtaining oscillatory motion of the beam axes is by mechanically scanning all of the plurality of transducers simultaneously. In this case, although mechanical movement of the transducers does introduce a limitation on the scanning rate, the effect of this limitation may be minimised by providing suitably switching means which require the transducers to scan only once while obtaining a complete cross-sectional visualisation. Thus, each transducer is activated in turn to direct a pulse of ultrasonic energy along the beam axis, the rate at which the transducers are activated being sufficiently fast, compared with the rate of mechanical oscillation of the transducers, that each transducer oscillates only a small distance between successive activation. thereof. The final result achieved by this method of operation is that at the end of a single mechanical scan, each of the transducers has been activated whilst it's beam was directed in all required directions.

The alternative means of obtaining oscillatory motion of the beam axes is by use of transducer arrays at each transducer position, the arrays being appropriately designed as to be capable of being steered electronically. In such a system there are no moving parts and the scanning rate obtainable with this system is limited only by considerations of electronic switching speeds and the rate of acquisition of ultrasonic information by the transducer after each transmitted pulse. Since such an array may be electronically steered to direct its beam in all required directions at a rate much faster than that possible when mechanical oscillation of the transducer is required, it is possible to operate this system by steering the beam from each transducer array to each of the required directions to measure the reflected echoes before activating the next transducer array and steering the beam from it to each of the required directions, and so on. It will, however, be appreciated that this plurality of transducer arrays capable of being electronically steered may also be operated in a manner similar to the operation of the mechanically oscillated transducers previously described.

Coupled with the oscillatory motion of the beam axes of the plurality of transducers, according to the present invention, the transducer array is moved relative to the object being examined. This movement is not the extensive movement necessary where a single transducer is used, where as previously described movement in a 150° arc around a patient or other object being examined is necessary, and in a typical embodiment of this invention the transducer array is moved over a distance corresponding to the distance between the individual transducers in the array. It will be apparent that this distance is considerably less than that of the whole array so that, when mechanically steerable transducers are used, the movement may be achieved within the one mechanical cycle of the transducers. alternatively, two or more varying types of movements may be employed, for example, with the transducer array moving half of the distance between the individual transducers and then returning to it's original position in association with one or more mechanical cycles of the transducers.

Other objects and features of the invention are illustrated in the accompanying drawings in which:

FIG. 2 is a schematic representation illustrating the manner in which a fuller representation of the object under examination is obtained in accordance with the present invention;

Figure 1:
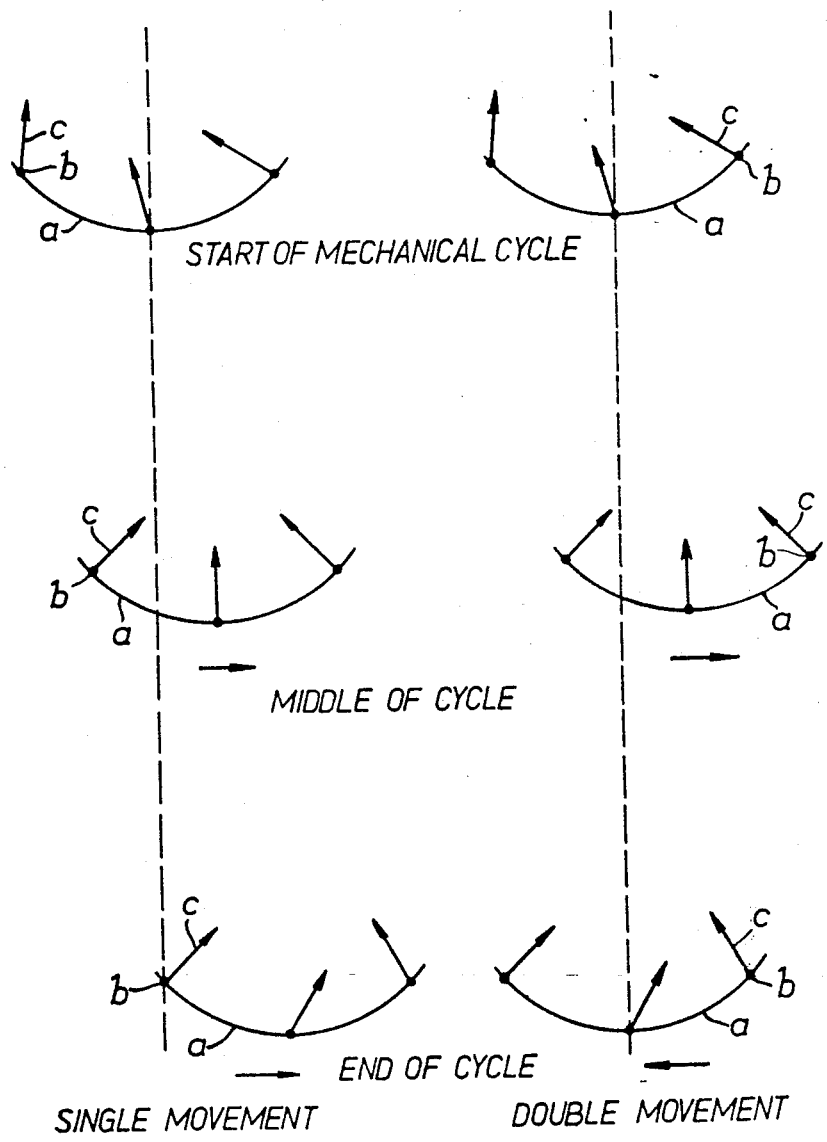
FIG. 1 is a schematic representation illustrating two modes of operation of ultrasonic examination equipment in accordance with the present invention.

FIG. 1 depicts schematically two alternative sequences of operation designated as "single" movement and "double" movement, respectively. For the purposes of illustration the transducer array $a$ is shown as comprising three individual transducers $b$ and the direction of the beam from each of the transducers $b$ is shown by the respective arrows $c$. The beam of each transducer $b$ moves in a scan from left to right as illustrated and in the "single" movement mode the array a is physically moved to the right a distance equal to the distance between individual transducers b during a single left-to-right scan of the transducers. In the "double" movement mode, the array a is moved to the right a distance equal to half the distance between the individual transducers b, and back to its original position, during a single left-to-right scan of the transducers.

Referring now to FIG. 2, there is depicted a situation which is experienced in practice where solid objects interfere in the examination of underlying objects. As previously mentioned this situation occurs by way of example in the ultrasonic examination of the liver where the patient's ribs may interfere with the examination. As depicted, where the transducer array (for the purpose of illustration shown as comprised of individual transducers A and B) is stationary, interfering structures result in areas being blocked from examination by the beams of ultrasonic energy emitted by the transducers. However, where the array is moved in accordance with the present invention, for example so that transducer A is moved to position A' and then to position A'' and transducer B is correspondingly moved to position B' and then to position B'', a fuller examination of the object is possible since areas previously blocked by the interfering structures are thereby exposed to the beams of ultrasonic energy emitted by the transducers.

Figure 3:
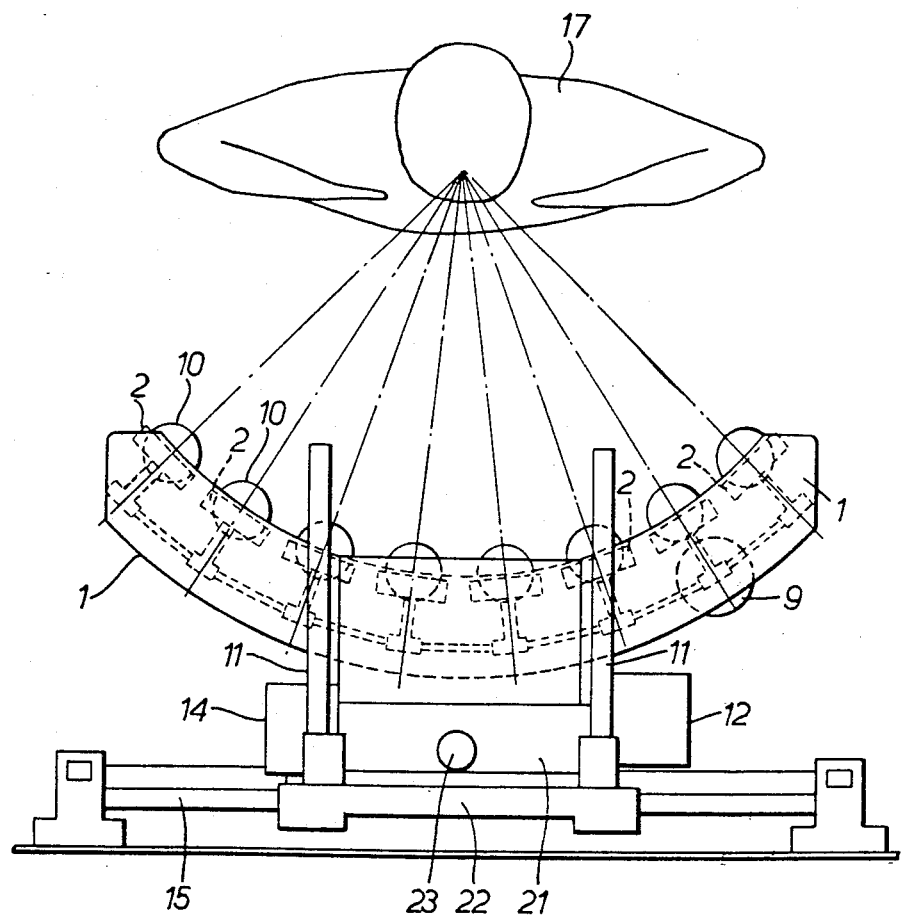
FIG. 3 illustrates ultrasonic examination apparatus in accordance with the present invention.
Figure 4:
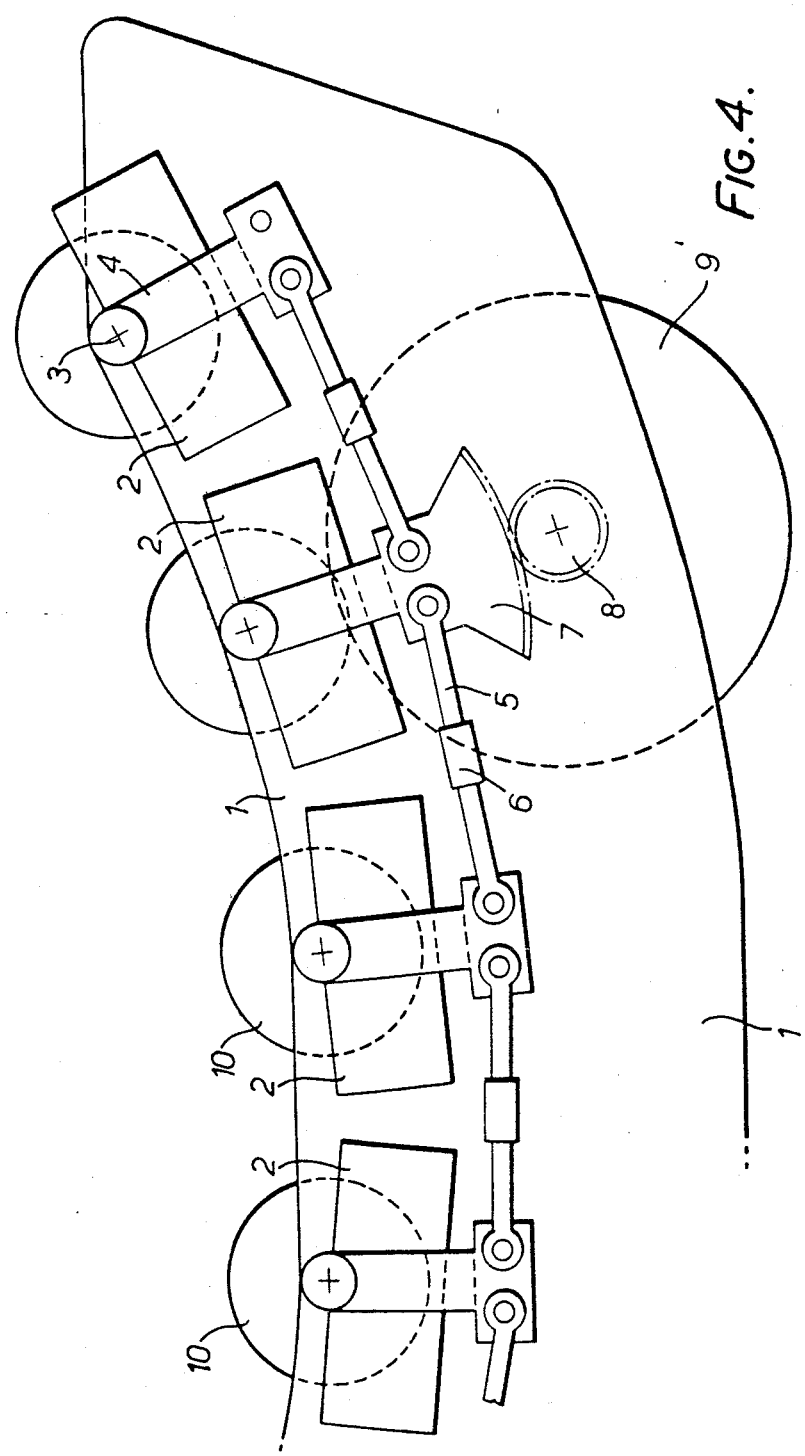
FIG. 4 illustrates in more detail the mechanism for oscillation of the transducers of the apparatus of FIG. 3.

The apparatus shown in FIGS. 3 and 4 comprises transducers 2 spatially mounted in a main supporting arm 1 so as to be capable of oscillating in a single plane, thereby directing the respective pulses of ultrasonic energy along a beam which is steerable in said plane. Eight transducers are shown by way of example however it will be appreciated that this number may be increased or decreased as desired. As shown in greater detail in FIG. 4, each transducer 2 is arranged to oscillate about pivot centre 3 by action of oscillator arm 4. The respective oscillator arms 4 of each of the transducers 2 are coupled by links 5 which are provided with adjusters 6 to enable accurate positioning of the transducers 2 with respect to each other and the arm 1. One of the oscillator arms 4 is provided with a sector gear 7 which meshes with a geared output 8 of motor 9, attached to arm 1. It will be apparent that rotation of the shaft 8 of the motor 9 will result in simultaneous pivoting of each of the transducers 2 about its pivot centre 3. The position or angle of each transducer is monitored by means of monitoring potentiometers 10.

Referring again to FIG. 3, main arm 1 is mounted on a main frame 21 which is slidable towards and away from the patient 17 to enable positioning of the transducers mounted on arm 1 relative to the patient. Frame 21 is slidable on pillars 11 and movement along these pillars is controlled by motor 12, for example, by means of a rack and pinion drive. Frame 21 is also mounted on a carriage 22 which slides along a track 15 controlled by motor 14, again by means of a rack and pinion drive or the like. The position of the carriage 22 relative to the track 15 is monitored by position monitoring potentiometer 23. As depicted, the apparatus enables movement of carriage 22 along track 15 in one or other of alternative sequences previously described whilst the transducers 2 are being scanned.

Figure 5:
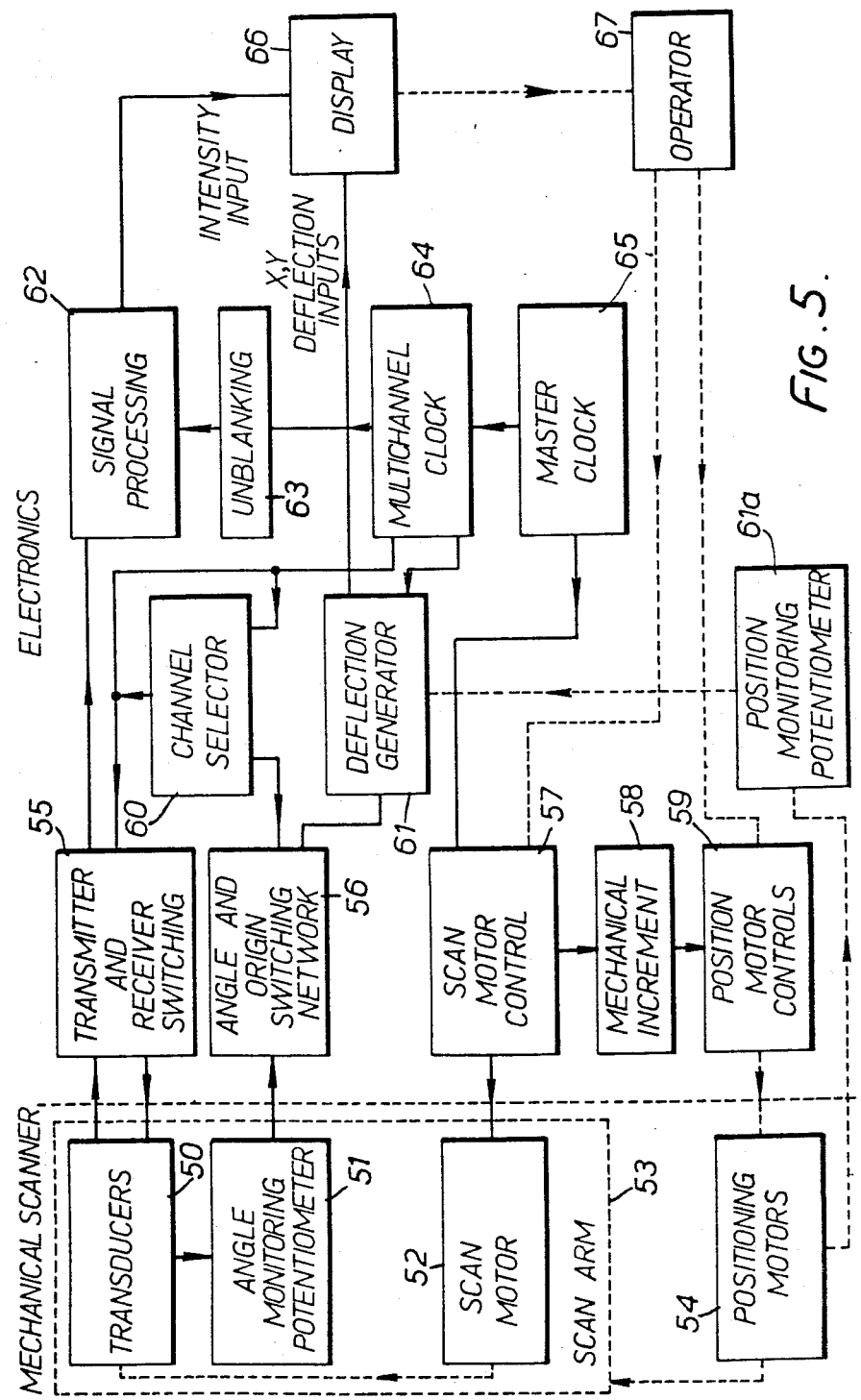
FIG. 5 shows a basic block diagram of one form of the electronics for the ultrasonic examination apparatus in accordance with the present invention.

As shown in FIG. 5, the master clock 65 provides basic time impulses to initiate multi-channel clock and to drive motors 52, 54 via the motor controller 57, 58, 59.

The multi-channel clock 64 outputs, in turn, trigger pulses to each channel upon receiving a pulse from the master clock 65.

The channel selector 60 counts trigger pulses and sends a binary channel address code to transmitter and receiver switching network 65 and to angle and origin switching network 56.

The signal processor 62 processes echoes from transmitter and receiver switching network 55, which echo signals are fed together with blanking pulses to the intensity modulation input of the display unit 66.

Deflection generator 61 generates X and Y deflection voltages from signals received from angle and origin switching network 56.

Figure 6:
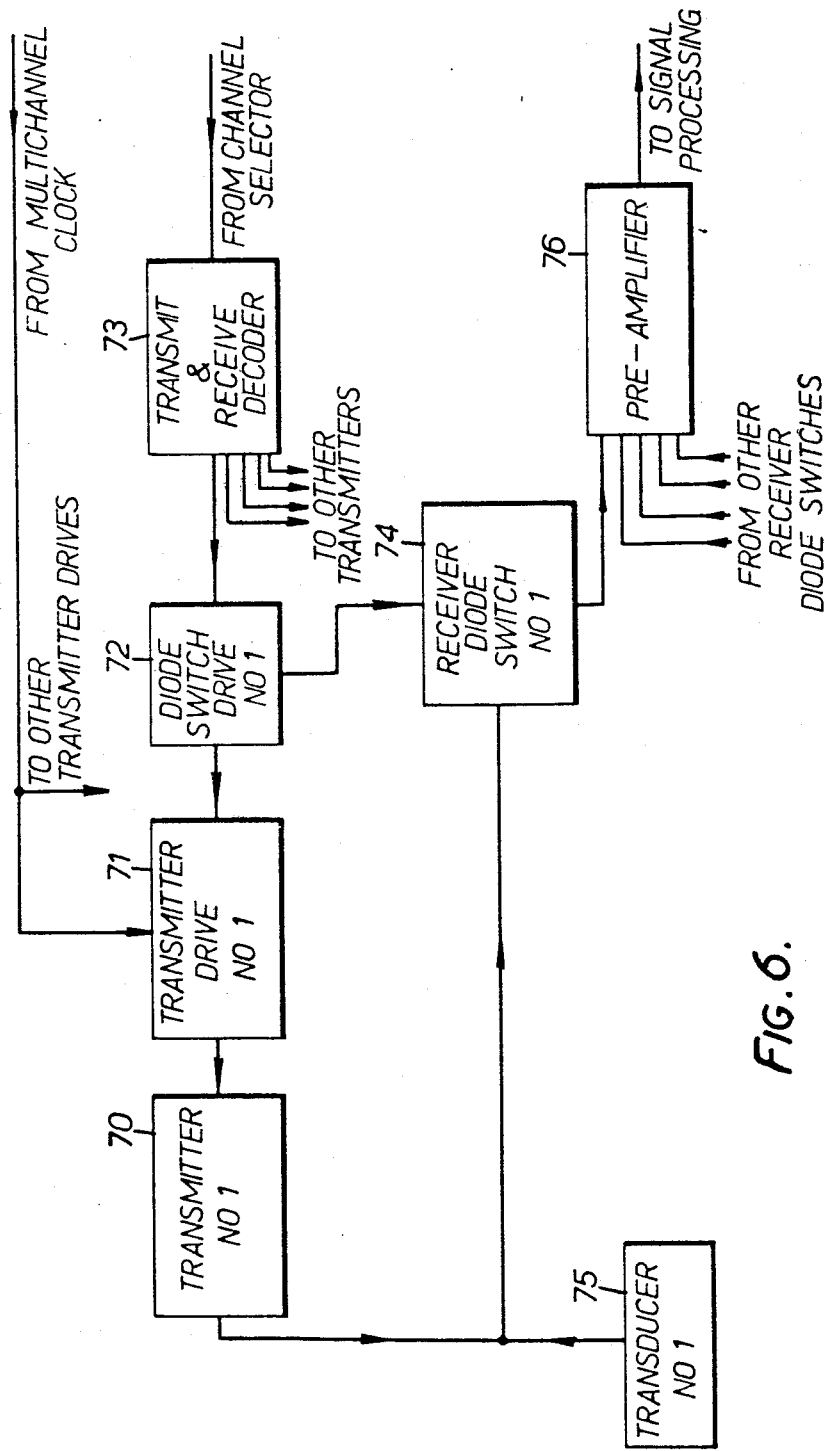
FIG. 6 shows a transmitter and receiver switching block diagram for the circuit of FIG. 5.

FIG. 6 shows transmitter and receiver switching network in greater detail. As seen in FIG. 6, transmit and receive decoder 73 decodes channel selector output signals from channel selector 60 to activate the correct diode switch drive 72 and transmitter drive 71. The multi-channel clock output then triggers the transmitter drive 71 to energize the transmitter 70.

Receiver diode switch 74 is energized by the decoder 73 via diode switch drive 72 which allows echo signals to pass to the preamplifier 76.

Figure 7:
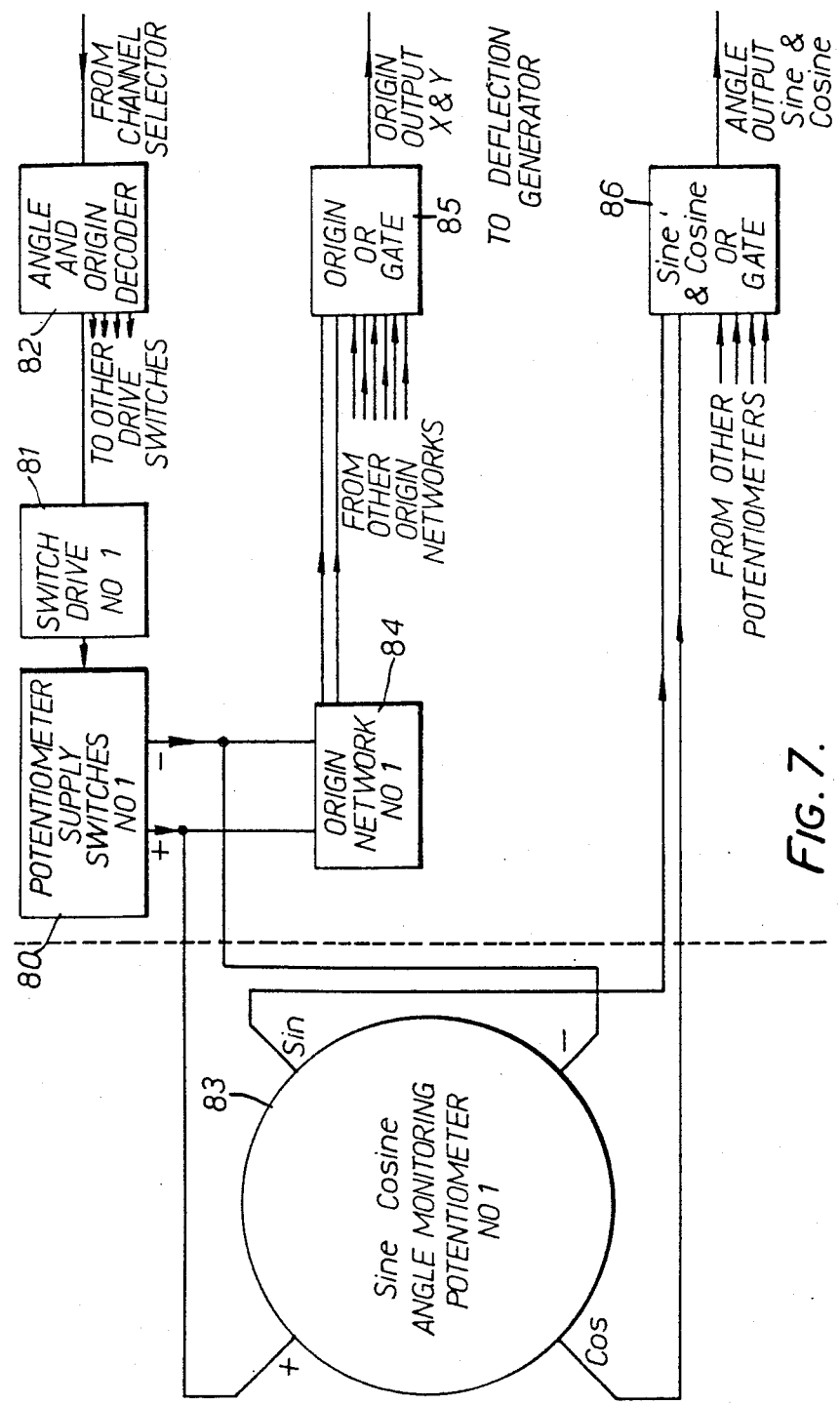
FIG. 7 shows a block diagram of an angle and origin switching network for the circuit of FIG. 5.

In FIG. 7, the angle and origin switching network 56 of FIG. 5 is more fully disclosed. As seen in FIG. 7, angle and origin decoder 82 decodes the channel selector output to activate the correct switch drive 81 and hence turn on the correct potentiometer supply switch 80. The supply switch 80 supplies reference voltages to the sine cosine angle monitoring potentiometer 83 and to the origin network 84.

The X and Y origin coordinates from the origin network 84 and the sine and cosine angle output from the potentiometer 83 are fed via their respective OR gates to the deflection generators 61 (see FIG. 5) within the processing electronics.

From the foregoing description it will therefore be appreciated that the present invention enables more rapid and complete scanning of an object subject to ultrasonic examination. While the invention has been described with reference to illustrative embodiments, it will be generally understood by those skilled in the art that various changes may be made and equivalents be substituted for elements thereof without departing from the true spirit and scope of the invention.

What I claim is:

1. Apparatus for the ultrasonic examination of an object comprising a plurality of transducers, each transducer being capable of directing pulses of ultrasonic energy along a beam into the said object and receiving echoes of said pulses reflected along said beam by acoustic impedance discontinuities in said object, said transducers being spatially positioned in a single plane relative to each other, means for steering each of said beams to a plurality of angular directions in said plane during examination of the object, means for moving said spatially positioned plurality of transducers in said plane relative to said object simultaneously with said steering of said beams, and means for sequentially activating each of said transducers to direct a pulse of ultrasonic energy along a beam into the object and to receive echoes reflected along said beam in each of said angular directions at a rate sufficiently fast, compared to the rate of movement of the transducer beams, that the beam of each transducer moves only a small distance between successive activations thereof.

2. Apparatus as defined in claim 1, wherein said means for steering the beams of said plurality of transducers comprises means for simultaneously mechanically oscillating said transducers.

3. Apparatus as defined in claim 2 wherein said plurality of transducers are mounted in a main arm for simultaneous mechanical oscillation about respective pivot centers.

4. Apparatus as defined in claim 3 further comprising a carriage supporting said main arm, said carriage being slidable relative to the object during examination of the object.

5. Apparatus as defined in claim 1, wherein said means for moving said plurality of transducers comprises means for moving said transducers through a distance corresponding to the distance between individual transducers during steering of the transducers to the plurality of angular directions.

6. Apparatus as defined in claim 1, wherein said means for moving said plurality of transducers comprises means for moving and returning said transducers through half the distance corresponding to the distance between individual transducers during steering of the transducers to the plurality of angular directions.

7. Apparatus as defined in claim 1, wherein each of said plurality of transducers comprises a multi-element array electronically steered to direct the beam to said plurality of angular directions.

8. Apparatus as defined in claim 7, further including means for activating each of said multi-element arrays in turn to direct a pulse of ultrasonic energy along a beam into the object and receive echoes reflected along said beam in all of said angular directions.

9. A method of ultrasonic examination of an object which comprises directing pulses of ultrasonic energy along a plurality of beams into said object and receiving echoes of said pulses reflected along said beams by acoustic impedance discontinuities in said object, said directing step including directing said beams into the object from positions spaced relative to each other in a single plane and steering each beam to a plurality of angular directions in said plane during examination of the object, the spaced positions from which said beams are directed being moved in said plane relative to said object simultaneously with said steering of said beams, and wherein said pulses are sequentially directed into the object and echoes received along each of said beams in each of said angular directions at a rate sufficiently fast, compared to the rate of movement of the beams that each beam moves only a small distance between successive activations thereof.

10. A method as defined in claim 8, wherein said positions are moved through a distance corresponding to the distance between individual positions, said movement being made during steering of the beams to the plurality of angular directions.

11. A method as defined in claim 9, wherein said positions are moved and returned through half the distance corresponding to the distance between individual positions, said movement being made during steering of the beams to the plurality of angular directions.

12. A method as defined in claim 9, wherein the pulses of ultrasonic energy are directed into said objects and echoes received by a plurality of spatially positioned transducers which are simultaneously mechanically oscillated.

13. A method as defined in claim 9, wherein the pulses of ultrasonic energy are directed into said object and echoes received by a plurality of spatially positioned transducers each comprising a multi-element array which is electronically steered.

14. A method as defined in claim 13, wherein said pulses are directed into the object and echoes received in turn along each of said beams in all of said angular directions.

* * * * *